United States Patent [19]

Parthasarathy et al.

[11] 4,309,355

[45] Jan. 5, 1982

[54] CATALYTIC OXIDATIVE DEHYDROGENATION OF ALKENES OR ALKADIENES TO FURAN COMPOUNDS

[75] Inventors: R. Parthasarathy; Eugene V. Hort, both of Wayne, N.J.

[73] Assignee: GAF Corporation, New York, N.Y.

[21] Appl. No.: 229,411

[22] Filed: Jan. 29, 1981

Related U.S. Application Data

[62] Division of Ser. No. 187,700, Sep. 16, 1980.

[51] Int. Cl.$^3$ .................................................. C07D 307/36
[52] U.S. Cl. .............................. 260/346.11; 252/435; 252/437; 252/467
[58] Field of Search ................................... 260/346.11

[56] References Cited

U.S. PATENT DOCUMENTS 3,238,225  3/1966  Brill et al. ..................... 260/346.11
4,278,563  7/1981  Fremont et al. ........... 260/346.11 X
4,280,959  7/1981  Parthasarathy et al. ....... 260/346.11

*Primary Examiner*—Richard Raymond
*Attorney, Agent, or Firm*—James Magee, Jr.; Walter Katz

[57] ABSTRACT

Alkenes and/or alkadienes are contacted with molecular oxygen and an oxidative dehydrogenation catalyst consisting essentially of silver, molybdenum and oxygen, and at least one promotor selected from the group consisting of phosphorus, arsenic, antimony and bismuth.

4 Claims, No Drawings

CATALYTIC OXIDATIVE DEHYDROGENATION OF ALKENES OR ALKADIENES TO FURAN COMPOUNDS

This is a division of application Ser. No. 187,700, filed Sept. 16, 1980.

BACKGROUND OF THE INVENTION

1. Field of the Invention

This invention relates to oxidative dehydrogenation catalysts and the use thereof for the conversion of alkenes and/or alkadienes to furan compounds.

2. Description of the Prior Art

Furan compounds can react readily with oxygen under oxidation conditions to produce ring cleavage and the formation of polymers. Accordingly, the production of furan compounds by the oxidative dehydrogenation of hydrocarbons has generally been avoided. Recently it has been discovered that furan compounds can be produced effectively by the oxidative dehydrogenation of hydrocarbons in the presence of certain specific catalysts. Accordingly, the search for additional catalysts suitable for this reaction continues.

The state of the prior art is exemplified particularly by U.S. Pat. Nos. 3,906,009, 3,894,055, 3,928,389, 3,912,763, 4,039,476 and 4,026,820. The catalyst systems disclosed in these patents, however, are not especially selective in forming only furan at moderate or high conversions. Instead, a considerable portion of the alkene or alkadiene starting material is converted to undesired aldehydes, ketones, or oxidized to carbon oxides and water.

Therefore, it is the object of the present invention to provide a new and improved oxidative dehydrogenation catalyst for the conversion of alkenes or alkadienes to furan compounds which is highly selective in oxidizing butadiene to furan in the vapor phase.

SUMMARY OF THE INVENTION

In accordance with the present invention, there is provided an improved catalyst for the production of furan type compounds from alkenes and alkadienes having from 4 to 10 carbon atoms, which catalyst consists essentially of silver, molybdenum and oxygen, and at least one promotor selected from the group consisting of phosphorus, arsenic, antimony and bismuth.

DETAILED DESCRIPTION OF THE INVENTION

The atom ratio of silver-to-molybdenum will generally be in the range of about 0.25:1 to about 10:1, preferably in the range of about 0.5:1 to about 6:1, and, in the best mode, in the range of about 1:1 to about 4:1. The atom ratio of the promotor to molybdenum suitably is in the range of 0.005:1 to 0.5:1, preferably in the range of 0.01:1 to about 0.3:1, and, in the best mode, in the range of 0.05:1 to about 0.1:1.

If desired, the novel, improved catalysts of the invention can be supported on conventional solid catalytic support materials, for example, zinc oxide, silica, alumina, boria, magnesia, titania, zirconia, and mixtures thereof. Where a catalyst support is employed, the support will generally constitute from about 10 to about 98, preferably from about 75 to about 95, weight percent of the total catalyst composition. Supports having a surface area in the range of about 2 to about 50 m$^2$/g, and preferably in the range of about 5 to about 20 m$^2$/g, are desirable.

The catalysts of the present invention can be prepared by a wide variety of techniques, for example, coprecipitation, impregnation, or aqueous or non-aqueous solution or suspension mixing. In the preferred embodiment of this invention, the catalyst is prepared by coprecipitation of water soluble silver and molybdenum salts, such as silver nitrate and ammonium heptamolybdate, followed by drying and calcination. Any compound of silver or molybdenum can be used in preparing the catalyst as long as all of the elements other than silver, molybdenum and oxygen are removed from the final catalyst by washing or by volatilization. However, trace amounts of other elements, such as alkali or alkaline earth and transitional metals, are not detrimental. Generally the preferred compounds of silver and molybdenum are those easily converted to the oxides on calcination. Examples of these are the nitrates, acetates and other carboxylates, hydroxides and the like. The promotors, too, may be introduced as a water soluble salt, or as an insoluble compound, such as the oxide or hydroxide.

Unsupported catalysts may be used as well. One technique for forming an unsupported catalyst comprises mixing one or more silver compounds, and one or more molybdenum compounds.

The compounds also can be admixed in the form of dry compounds and then calcined. They can be mixed in the presence of a diluent to form a paste and/or one of the components can be employed in liquid form, such as phosphoric acid, to form the paste. If desired, the paste can be dried before calcining. A particle forming step, such as pelletizing or screening, can precede the drying step or the calcining step.

Generally the catalyst is prepared by coprecipitation, e.g. by admixing aqueous solutions of silver nitrate and ammonium heptamolybdate together with a soluble salt of the promotor element. In this process, the pH of the slurry is maintained in the range of about 5.5–7.0 and the resulting precipitate is washed free of ammonium nitrate. Then a suitable diluent, such as a fine particle α-Al$_2$O$_3$, is added and the paste is dried and calcined. A particle forming step, such as pelletizing or pilling, may precede the drying or calcination, if desired.

In another technique, silver molybdate is precipitated and the oxide or hydroxide or other insoluble compound convertible to oxide of the promotor element is blended in.

The calcining step itself comprises heating the catalyst composition to a temperature in the range of about 250° C. to about 650° C. for about 0.5 to about 24 hours preferably at a temperature range of 400° C. –600° C. for about 2–16 hrs., in the presence of an oxygen-containing gas, such as air.

Suitable feeds for conversion to furan compounds include the unsaturated acyclic hydrocarbons, particularly the acyclic alkenes and acyclic alkadienes having from 4 to 10 carbon atoms. Examples include n-butene-1, butene-2, n-pentene-1, isopentene, hexene-1, heptene-2, octene-1, decene-1, 2-methylbutene-1, hexene-3, 2-ethylbutene-1, 2-methylpentene-3, 3-ethylhexene-2, butadiene-1,3, pentadiene-1,3, isoprene, hexadiene-1,3, decadiene-1,3, pentadiene-1,3, and the like, and mixtures thereof. The acyclic alkadienes having from 4 to 5 carbon atoms are presently preferred.

The furan compounds produced by the process of the present invention have the formula:

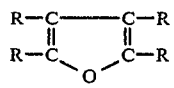

wherein each R is individually selected from the group consisting of hydrogen and alkyl radicals having from 1 to 6 carbon atoms, the total carbon atoms in the R radicals being in the range of 0 to 6. Representative products include furan, 2-methylfuran, 3-methylfuran, 2,5-diethylfuran, 2-n-hexylfuran, 2-isopropyl-3-methylfuran, 3,4-di(n-propyl)furan, 3-methyl-4-n-butylfuran and the like.

In the process, a hydrocarbon feed comprising of one or more acyclic alkenes and/or one or more acyclic alkadienes is contacted under suitable reaction conditions with oxygen-containing gas for conversion to furan compounds in the presence of the above-defined catalyst. The temperature used is in the range of 200° C. to 600° C., preferably in the range of 250°–450° C. Any suitable pressure can be employed, but, in general, the pressure ranges from 0.05 to about 200 psig. and preferably in the range of about 0.1 to 25 psig. The total gas rate may be in the general range of about 50 to 5000 standard volumes per hour per volume of catalyst bed (GHSV) and preferably in range of about 100 to 4000 (GHSV). The mol ratio of oxygen to alkenes and alkadienes will generally be in the range of about 0.1:1 to about 10:1, and preferably in the range of 0.5:1 to about 6:1. Steam can be employed in the reaction zone as an inert diluent and a heat carrier, suitably in the mol ratio of steam to alkenes and alkadienes of about 0.5:1 to 50:1, and preferably from about 5:1 to about 25:1.

The alkenes, if present, are converted mostly to corresponding alkadienes, which, in turn, are converted in significant quantities to furan compounds. However, the reaction effluent can also contain unreacted feed material, lower alkenes, such as ethylene and propylene; water, oxides of carbon, aldehydes, such as crotonaldehyde, acetaldehyde and acrolein; ketones, such as acetone, methyl ethyl ketone and methyl vinyl ketone; and other oxygenated products. Uncoverted alkenes and/or alkadienes can be recovered and recycled to the reactor as can other partial oxygenated products, such as crotonaldehyde, which are convertible to furan compounds under the reaction conditions.

The following examples are presented in further illustration of the invention and should not be construed in undue limitation thereof.

PREPARATION OF CATALYSTS

EXAMPLE 1

BISMUTH-PROMOTED SILVER MOLYBDATE 2.43 g (5 mmols) of bismuth nitrate and 17.0 g (0.1 mol) silver nitrate were dissolved with gentle warming in 25 ml water acidified with 2 ml conc. $HNO_3$. Then 8.83 g (0.05 mol Mo) of ammonium heptamolybdate dissolved in 15 ml water containing 3 ml $NH_4OH$ as added dropwise with continuous stirring to the mixed bismuth-silver nitrate solution. After the precipitation, was completed, 5.75 g of fine particle $\alpha$-$Al_2O_3$ was blended in, the mixture evaporated to dryness, heated for ½ hour at 120°, and calcined for 2 hours at 500°, and for 3 hrs. at 600°. The mass then was ground to 2 to 4 mm particles for evaluation in a flow reactor. The g.-atomic ratio, Bi/Mo, was 0.1 and Ag/Mo was 2.0.

EXAMPLE 2

Phosphorous-Promoted Silver Molybdate

A solution of 8.83 g ammonium heptamolybdate in 15 ml water made ammoniacal with 3 cc $NH_4OH$ was added dropwise to a solution of 17 g. silver nitrate in 15 ml water. The resulting precipitate was washed three times with 20 ml portions of distilled water and a solution of 1.2 g. $H_3PO_4$ (85%) in 10 ml water was added with stirring. Then 5.6 g of $\alpha$-$Al_2O_3$ was blended in and mass was evaporated to dryness over a steam bath, dried further at 120°, and calcined at 500° C. for 3 hours and ground to 2–4 mm particles. The g.-atomic ratio of Ag/P was 0.1 and Ag/Mo was 2.0.

EXAMPLE 3

Arsenic-Promoted Silver Molybdate

A washed silver molybdate precipitate was prepared as in Example 2. Then a slurry of 0.5 g arsenic trioxide in 10 ml of conc. $NH_4OH$ was mixed uniformly into the washed precipitate and the mass was evaporated to dryness over a steam bath and finally dried at 120°. The mass was then calcined for 3 hrs. at 400° C. and commutated. The g.-atomic ratio of As/Mo was 0.1 and Ag/Mo was 2.0.

EXAMPLE 4

Antimony-Promoted Silver Molybdate

This catalyst was prepared as in Example 3 using 2.92 g. of antimony trioxide in place of arsenic trioxide. The g. atom ratio of Sb/Mo was 0.1 and Ag/Mo was 2.0.

Other catalyst compositions containing the promotor elements in g. atomic ratios to molybdenum in the range 0.05:1 to 0.25:1, and Ag to Mo atom ratios of 2, were prepared similarly.

EXAMPLE 5

Process Reaction

The reaction vessel, a stainless steel tube 12 inches in length, with a 1 inch i.d., and having a ⅛" central thermal well about 2–10 ml of catalyst was charged into the reactor. Both butadiene and 1-butene were used as hydrocarbon feed materials. Up to 50% nitrogen was used as a diluent.

The reaction was continued for several hours whereupon steady state conditions were reached. The process results was recorded under such conditions.

In the table below the terms used are defined as follows:

Conversion: Percentage of starting material, e.g. butadiene, consumed in the reaction.

Selectivity: Percentage of a particular product, e.g. furan, produced in the process, based on the total starting material consumed.

Aldehydes: Acetaldehyde, acrolein crotonaldehyde.

Other: Acetone and $C_4$-ketones.

Carbon oxides: CO and $CO_2$. $C_4^=$: Butadiene or 1-Butene.

TABLE

| Catalyst | Calc'n (Hrs., °C.) | | Operating Conditions | | Temp. (°C.) | % $C_4^=$ Conv | Furan % | Carbon Oxide % | Aldehydes % | Other |
|---|---|---|---|---|---|---|---|---|---|---|
| | | $O_2/C_4^=$ | Contact Time (Secs) | | | | | | | |
| $Ag_2$—$P_{0.1}$—Mo | 3 | 500 | 1-2 | 1 | 400 | 31 | 32 | 64 | 4 | * |
| $Ag_2$—$As_{0.1}$—Mo | 3 | 400 | 1-2 | 2-4 | 420 | 31 | 40 | 52 | 6 | |
| $Ag_2$—$Sb_{0.05}$—Mo | 3 | 538 | 1-2 | 2-4 | 352 | 19 | 33 | 61 | 6 | |
| $Ag_2$—$Bi_{0.1}$—Mo | 3 | 600 | 1-2 | 7-8 | 483 | 35 | 29 | 62 | 7 | |
| $Ag_2$—$Bi_{0.05}$—Mo | 3 | 400 | 1-2 | 2-4 | 353 | 35 | 25 | 65 | 10 | |
| $Ag_2$—Mo | 3 | 400 | 1-2 | 1.5 | 376 | 21 | 21 | 71 | 8 | |
| $Ag_{2.5}$—$As_{0.1}$—Mo | 3 | 400 | 3 | 2 | 415 | 6 | 35 | 60 | 5 | 1-Butene feed |
| $Ag_{2.5}$—Mo | 3 | 538 | 2 | 2 | 360 | 27 | 2 | 25 | 2 | 72* |

*Butadiene Product

The results show an effective and selective conversion to furan, particularly with a butadiene feed, under steady state conditions, using the promoted catalyst, as compared to silver molybdate alone. While this effect is not completely understood at present, it is believed that the promotor elements act as a poison in silver molybdate to retard side reactions which lead to deep oxidation, while enhancing the desirable furan-forming reaction.

What is claimed is:

1. A process which comprises reacting at least one unsaturated acyclic feed hydrocarbon selected from the group consisting of alkenes and alkadienes having 4 to 10 carbon atoms, with oxygen in contact with a catalyst composition consisting essentially of silver molybdenum and oxygen, and at least one promotor selected from the group consisting of phosphorus, arsenic, antimony and bismuth, with the silver to molybdenum atom ratio being in the range of 0.25:1 to about 10:1, and the promotor to molybdenum atom ratio being in the range of 0.005:1 to 0.5:1 under suitable vapor-phase reaction conditions for the conversion of said at least one unsaturated acyclic feed hydrocarbon to at least one furan compound having the formula

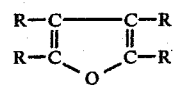

wherein each R is individually selected from the group consisting of hydrogen and alkyl radicals having from 1 to 6 carbon atoms, the total carbon atoms in the R radicals being in the range of 0 to 6; and recovering at least a portion of the furan compounds thus produced.

2. A process in accordance with claim 1 wherein said feed hydrocarbon comprises butadiene.

3. A process according to claim 1 wherein said silver to molybdenum atom ratio is in the range of about 0.5:1 to about 6:1, and said promotor to molybdenum atom ratio is in the range of about 0:01:1 to 0:3:1.

4. A process according to claim 1 wherein said silver to molybdenum atom ratio is in the range of about 1:1 to about 4:1, and said promotor to molybdenum atom ratio is in the range of about 0.05:1 to 0.1:1.

* * * * *